United States Patent [19]
Furukawa et al.

[11] Patent Number: 5,776,942
[45] Date of Patent: Jul. 7, 1998

[54] BRONCHODILATING PYRIDO[2,3-D] PYRIMIDINE DERIVATIVES

[75] Inventors: Kazuhito Furukawa; Taisuke Hasegawa, both of Katoh-gun, Japan

[73] Assignee: Nippon Zoki Pharmaceutical Co., Ltd., Osaka, Japan

[21] Appl. No.: 490,297

[22] Filed: Jun. 14, 1995

[30] Foreign Application Priority Data

Jun. 17, 1994 [JP] Japan .................................. 6-159322
Jun. 17, 1994 [JP] Japan .................................. 6-159323
Jun. 17, 1994 [JP] Japan .................................. 6-159324

[51] Int. Cl.$^6$ ..................... C07D 239/00; A61K 31/505
[52] U.S. Cl. ........................................ 514/279; 544/258
[58] Field of Search ........................ 544/279; 514/258

[56] References Cited

U.S. PATENT DOCUMENTS

| | | | |
|---|---|---|---|
| 3,272,816 | 9/1966 | Papesch | 514/258 |
| 3,275,634 | 9/1966 | Papesch | 514/48 |
| 4,808,587 | 2/1989 | Go et al. | 514/258 |

FOREIGN PATENT DOCUMENTS

| | | |
|---|---|---|
| 0 243 311 B1 | 6/1993 | European Pat. Off. |
| 2317230 | 10/1973 | Germany |
| 2334266 | 1/1974 | Germany |
| 63-45279 | 2/1988 | Japan |
| 989048 | 4/1965 | United Kingdom |
| WO 92/08719 | 5/1992 | WIPO |

OTHER PUBLICATIONS

Chemical Abstracts, vol. 102, No. 15, (15 Apr. 1985) pp. 625–626, abstract No. 131985x; T. L. Su, et al., "Pyrimidines, 21. Novel reactions of 5–cyano–1,3–dimethyluracil with carbon nucleophiles. A facile preparation of certain pyrido(2,3–d)pyrimidines".

Chemical Abstracts, vol. 93, No. 9 (1 Sep. 1980) pp. 643–644, abstract No. 95234m; S. Brunel, et al.: "Synthesis of new 1H,3H–pyrido(2,3–d)pyrimidine–2,4–diones".

Chemical Abstracts, vol. 100, No. 9 (27 Feb. 1984) p. 596, abstract No. 68254z, T. Itoh, et al.: "A simple synthesis of 1,3–dialkylpyrido(2,3–d)pyrimidines".

Tominaga, et al., Chemical Abstracts, vol. 100, No. 209737y (1984).

Matyus, et al., Chemical Abstracts, vol. 102, No. 6405g (1985).

Rodgers, et al., Chemical Abstracts, vol. 106, No. 156415g (1987).

Chemical and Pharmaceutical Bulletin, vol. 33, No. 4, 1985, pp. 1375–1379; T. Itoh, et al.: "A simple synthesis of 1,3–dialkylpyrido(2,3–d)pyrimidines".

McLean, et al., *J. Chem. Soc.*, pp. 2582–2585 (1949).

Cherdantseva, N.M., et al., "Synthesis of pyrido[2,3–d] pyrimidines on the basis of 5–formyl–6–aminouracils", Chem. Heterocycl. Compounds, vol. 19, No. 6, 1983, pp. 674–677.

Rodgers, G.R., et al., "Linear expanded xanthines", Monatshefte fur Chemie (Chemical Monthly), vol. 117, 1986, pp. 879–882.

Burova, O.A., et al., "Pyrido[2,3–d]pyrimidines. 7. Reactions of 1,3–dimethyl–5, 7–dichloro–6–nitropyrido[2,3–d] pyrimidine–2,4–dione with amines. Synthesis of derivatives of triazolo(4',5':4,5)pyrido[2,3–d]pyrimidine", Chem. Heterocycl. Compounds, vol. 29, No. 3, 1993, pp. 335–338.

Heber, D., et al., "Synthesis and positive inotropic activity of several 5–aminopyrido[2,3–d]pyrimidines", Die Pharmazie, vol. 48, No. 7, Jul. 1993, pp. 509–513.

Heber, D., et al., "Positive inotropic activity of 5–amino–6–cyano–1,3–dimethyl–1,2,3,4–tetrahydropyrido [2,3–d]pyrimidine–2,4–dione in cardiac muscle from guinea–pig and man", Die Pharmazie, vol. 48, No. 7, Jul. 1993, pp. 537–541.

Goto, et al., "Anti–anaphylactic activities of a new benzopyranopyridine derivative Y–12,141 in rats and guinea pigs", Japan. J. Pharmacol. 30, 1980, pp. 537–547.

Su, et al., "Pyrimidines, 21. Novel reactions of 5–cyano–1, 3–dimethyluracil with carbon nucleophiles. A facile preparation of certain pyrido[2,3–d]pyrimidines (1)", J. Heterocycl. Chem. 1984, 21, pp. 1543–1547.

*Primary Examiner*—Matthew V. Grumbling
*Attorney, Agent, or Firm*—Fisher, Christen & Sabol

[57] ABSTRACT

A rapid-acting remedy for asthma having a bronchodilating action contains at least one pyrido[2,3-d]pyrimidine derivative represented by the general formula (A) or pharmaceutically acceptable salts or metal complexes thereof as an effective component:

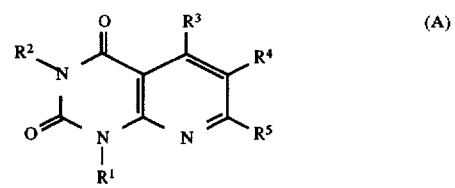

(A)

wherein $R^1$ and $R^2$ are the same or different and each of $R^1$ and $R^2$ is hydrogen, alkyl or benzyl; $R^3$ is hydrogen, hydroxyl, dialkylaminomethyleneamino or —NH—X; X is hydrogen, alkyl, alkenyl, hydroxyl, amino, hydroxyalkyl, benzyl or acyl; $R^4$ is hydrogen, alkyl, halogen, nitro, amino, hydroxyl, benzyloxy, cyano, carboxyl, alkoxycarbonyl, alkoxysulfonyl, aminosulfonyl, dialkylaminosulfonyl or sulfo; and $R^5$ is hydrogen, alkyl or amino. The rapid-acting remedy for bronchial asthma is capable of relieving the symptom of laboring breath at the onset of asthma due to its excellent bronchodilating action. It can be used as a therapy not only for allergic asthma but also for various bronchial asthmas such as endogenous asthma, exogenous asthma and dust asthma.

20 Claims, No Drawings

BRONCHODILATING PYRIDO[2,3-D] PYRIMIDINE DERIVATIVES

FIELD OF THE INVENTION

The present invention relates to a remedy for bronchial asthma containing pyrido[2,3-d]pyrimidine derivatives or pharmaceutically acceptable salts thereof as an effective component.

BACKGROUND OF THE INVENTION

In modern society, there has been an increase in the number of patients suffering from bronchial asthma as an influence of an increase in automobiles for example. Bronchial asthma is a disease causing a spasticity of bronchial smooth muscles upon its onset and the patient is in a state of a very labored dyspnea upon onset. It is classified into atopic, infectious and mixed bronchial asthma depending upon the cause for the onset. It is believed that, usually, the so-called preparatory state for asthma is established by: (1) addition of an acquired factor to the constitutional factor such as an acceleration of airway hypersensitivity to chemical mediators or other factors and, then (2) other predispositions such as an antigen stimulation are participated therein.

With respect to pharmaceutical agents for bronchial asthma, antiallergic agents, expectorants, adrenocortical steroids and tranquilizers have been used besides bronchodilators which directly act upon the contracted bronchus to relax it. The antiallergic agent which is one of the commonly used agents therefor is that which inhibits the liberation or the synthesis of chemical mediators such as histamine which participate in allergy or antagonize against it. Thus, such an antiallergic agent is not a direct therapeutic agent wherein the contracted airway upon onset is dilated for relieving difficulty in breathing. It is used as a drug which prevents the onset of the asthma symptom associated with a chemical mediator. On the other hand, a bronchodilator is used as a rapid-acting therapeutical agent for relieving the symptom of laboring breath upon the onset of asthma.

The pyrido[2,3-d]pyrimidine derivatives described in Japanese Laid-Open Patent Publication Sho-63/45279 and corresponding U.S. Pat. No. 4,808,587 exhibit an antiallergic action based upon an antagonistic action or liberation-inhibiting action against the chemical mediators such as histamine as apparent from the description of the pharmacological test (PCA test).

The present inventors have conducted a continued investigation on substances exhibiting a bronchodilating action which is effective as a rapid-acting remedy upon onset of asthma and found that certain pyrido[2,3-d]pyrimidine derivatives have an excellent bronchodilating action whereupon the present invention has been achieved.

SUMMARY OF THE INVENTION

The present invention provides pyrido[2,3-d]pyrimidine derivatives which exhibit excellent bronchodilating action. Compounds of the present invention in addition to preventing the onset of asthma symptoms involving chemical mediators such as histamine, are also capable of dilating the contracted bronchus and of remedying the laboring breath of asthma. Thus, the present invention provides a rapid-acting agent which directly acts on the contracted tracheal smooth muscle to relax it to relieve difficulty in breathing. The compounds are highly effective as a bronchodilator which can be used as a remedy not only for allergic asthma but also for various types of bronchial asthma such as endogenous asthma, exogenous asthma and dust asthma.

The pyrido[2,3-d]pyrimidine derivatives which are contained as an effective component in the pharmaceutical compositions for remedying bronchial are compounds represented by the following general formula (A):

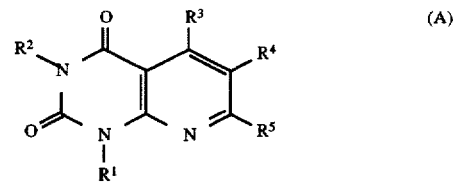

wherein $R^1$ and $R^2$ may be the same or different and each of $R^1$ and $R^2$ may be hydrogen, alkyl or benzyl; $R^3$ is hydrogen, hydroxyl, dialkylaminomethyleneamino or —NH—X; X is hydrogen, alkyl, alkenyl, hydroxyl, amino, hydroxyalkyl, benzyl or acyl; $R^4$ is hydrogen, alkyl, halogen, nitro, amino, hydroxyl, benzyloxy, cyano, carboxyl, alkoxycarbonyl, alkoxysulfonyl, aminosulfonyl, dialkylaminosulfonyl or sulfo; and $R^5$ is hydrogen, alkyl or amino.

The derivatives of the present invention also include pharmaceutically acceptable salts and metal complexes of the compounds represented by general formula (A). The present invention also provides pharmaceutical compositions containing pharmaceutically effective amounts of at least one of said derivatives as an effective component.

The pyrido[2,3-d]pyrimidine derivatives of the present invention exhibit both excellent bronchodilating and antiallergic actions and are quite useful as agents for treatment of various allergic diseases such as allergic rhinitis, allergic conjunctivitis, urticaria, allergic skin diseases, etc. as well as for bronchial asthma. In addition, compounds having a substituent other than hydrogen at the 7-position exhibit unexpectedly prolonged inhibitory action against bronchial contraction. Accordingly, they may be administered less frequently or in reduced dosages without loss of efficacy.

DETAILED DESCRIPTION OF THE INVENTION

The present invention provides a rapid-acting remedy for bronchial asthma which is capable of relieving the symptom of laboring breath as a result of its bronchodilating action at the onset of bronchial asthma.

The pyrido[2,3-d]pyrimidine derivatives which are contained as an effective component in the remedy for bronchial asthma of the present invention are compounds represented by the following general formula (A):

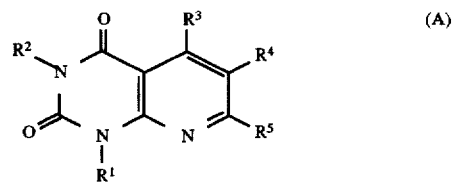

In the above general formula (A), $R^1$ and $R^2$ may be the same or different and each of $R^1$ and $R^2$ may be hydrogen, alkyl or benzyl; $R^3$ may be hydrogen, hydroxyl, dialkylaminomethyleneamino or —NH—X; X is hydrogen, alkyl, alkenyl, hydroxyl, amino, hydroxyalkyl, benzyl or acyl; $R^4$ may be hydrogen, alkyl, halogen, nitro, amino, hydroxyl, benzyloxy, cyano, carboxyl, alkoxycarbonyl, alkoxysulfonyl, aminosulfonyl, dialkylaminosulfonyl or sulfo; and $R^5$ may be hydrogen, alkyl or amino.

In the above general formula (A), examples of the alkyl for $R^1$ or $R^2$ are linear or branched alkyls having one to six carbon atoms such as methyl, ethyl, propyl, isopropyl, butyl, isobutyl, sec-butyl, tert-butyl, pentyl, isopentyl, neopentyl, tert-pentyl, hexyl and dimethylbutyl.

Examples of the alkyl in the dialkylaminomethyleneamino for $R^3$ are linear or branched alkyls having one to four carbon atoms such as methyl, ethyl, propyl, isopropyl, butyl, isobutyl, sec-butyl and tert-butyl. Examples of the alkyl for X in —NH—X for $R^3$ are linear or branched alkyls having one to four carbon atoms such as ethyl, propyl, isopropyl, butyl, isobutyl, sec-butyl and tert-butyl. Examples of the alkenyl for X are linear or branched alkenyl groups having two to four carbon atoms such as ethenyl, 1-propenyl, 2-propenyl, 1-butenyl, 2-butenyl, 3-butenyl and sec-butenyl. Examples of the hydroxyalkyl for X are those wherein at least one hydroxyl group is substituted on a linear or branched alkyl having one to four carbon atoms such as methyl, ethyl, propyl, isopropyl, butyl, isobutyl, sec-butyl and tert-butyl. Examples of the acyl for X are linear or branched acyl groups having one to four carbon atoms such as formyl, acetyl, propionyl, butyryl, isobutyryl and tert-butyryl as well as benzoyl.

Examples of the alkyl for $R^4$ are linear or branched alkyls having one to four carbon atoms such as methyl, ethyl, propyl, isopropyl, butyl, isobutyl, sec-butyl and tert-butyl. Examples of the halogen therefor are fluorine, chlorine, bromine and iodine. Examples of the alkoxycarbonyl for $R^4$ are carbonyls to which a linear or branched alkoxyl having one to four carbon atoms is bonded such as methoxy, ethoxy, propoxy, isopropoxy, butoxy, isobutoxy, sec-butoxy and tert-butoxy. Examples of the alkoxysulfonyl for $R^4$ are sulfonyls to which the above-mentioned linear or branched alkoxyl is bonded. Examples of the alkyl in the dialkylaminosulfonyl for $R^4$ are linear or branched alkyls having one to four carbons such as methyl, ethyl, propyl, isopropyl, butyl, isobutyl, sec-butyl and tert-butyl.

Examples of the alkyl for $R^5$ are linear or branched alkyls having one to four carbon atoms such as methyl, ethyl, propyl, isopropyl, butyl, isobutyl, sec-butyl and tert-butyl.

Among the above-mentioned compounds represented by the general formula (A), the following compounds are novel substances and, since they exhibit both bronchodilating and antiallergic actions, they are very useful as therapeutic and preventive agents for various allergic diseases, bronchial asthma, etc.:

1) A compound represented by the general formula (1):

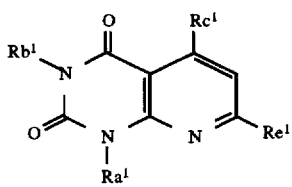

(1)

wherein $Ra^1$ and $Rb^1$ may be the same or different and each of $Ra^1$ and $Rb^1$ is alkyl; $Rc^1$ is amino or alkylamino; and $Re^1$ is alkyl.

2) A compound represented by the general formula (2):

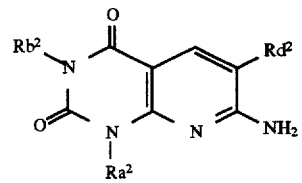

(2)

wherein $Ra^2$ and $Rb^2$ may be the same or different and each of $Ra^1$ and $Rb^2$ is alkyl; and $Rd^2$ is alkoxycarbonyl.

3) A compound represented by the general formula (3):

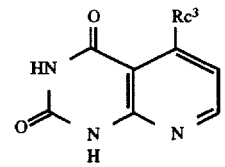

(3)

wherein $Rc^3$ is amino or benzylamino.

4) A compound represented by the general formula (4):

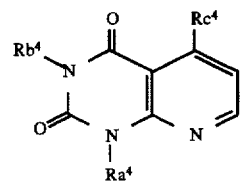

(4)

wherein one of $Ra^4$ and $Rb^4$ is hydrogen while the other is alkyl; and $Rc^4$ is amino or alkylamino.

5) A compound represented by the general formula (5):

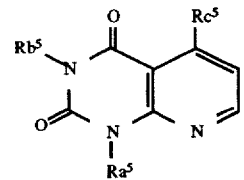

(5)

wherein $Ra^5$ and $Rb^5$ are different alkyl groups; and $Rc^5$ is amino or alkylamino.

6) A compound represented by the general formula (6):

(6)

wherein $Ra^6$ is hydrogen or alkyl; and $Rc^6$ is amino, alkylamino or benzylamino.

7) A compound represented by the general formula (7):

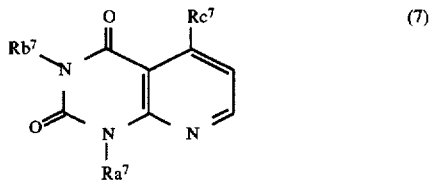

wherein $Ra^7$ and $Rb^7$ may be the same or different and each of $Ra^7$ and $Rb^7$ is alkyl; and $Rc^7$ is acylamino, alkylamino, benzylamino or dialkylaminomethyleneamino.

8) A compound represented by the general formula (8):

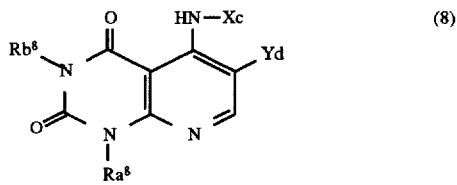

wherein $Ra^8$ and $Rb^8$ may be the same or different and each of $Ra^8$ and $Rb^8$ is alkyl; Xc is hydrogen, alkyl or acyl; and Yd is alkyl, halogen, nitro, amino, hydroxyl, benzyloxy, cyano, carboxyl, alkoxycarbonyl, alkoxysulfonyl, aminosulfonyl, dialkylaminosulfonyl or sulfo.

In the above-mentioned general formula (1), examples of the alkyl for $Ra^1$ or $Rb^1$ are linear or branched alkyls having one to four carbon atoms such as methyl, ethyl, propyl, isopropyl, butyl, isobutyl, sec-butyl and tert-butyl. Examples of the alkyl in the alkylamino for $Rc^1$ are linear or branched alkyls having one to four carbon atoms such as methyl, ethyl, propyl, isopropyl, butyl, isobutyl, sec-butyl and tert-butyl. Examples of the alkyl for $Re^1$ are linear or branched alkyls having one to four carbon atoms such as methyl, ethyl, propyl, isopropyl, butyl, isobutyl, sec-butyl and tert-butyl.

In the above-mentioned general formula (2), examples of the alkyl for $Ra^2$ or $Rb^2$ are linear or branched alkyls having one to four carbon atoms such as methyl, ethyl, propyl, isopropyl, butyl, isobutyl, sec-butyl and tert-butyl. Examples of the alkoxy in the alkoxycarbonyl for $Rd^2$ are linear or branched alkoxy groups having one to four carbon atoms such as ethoxy, propoxy, isopropoxy, butoxy, isobutoxy, sec-butoxy and tert-butoxy.

In the above-mentioned general formula (3), examples of the alkyl in the alkylamino for $Rc^3$ are linear or branched alkyls having one to four carbon atoms such as methyl, ethyl, propyl, isopropyl, butyl, isobutyl, sec-butyl and tert-butyl.

In the above-mentioned general formula (4), examples of the alkyl for $Ra^4$ or $Rb^4$ are linear or branched alkyls having one to four carbon atoms such as methyl, ethyl, propyl, isopropyl, butyl, isobutyl, sec-butyl and tert-butyl. Examples of the alkyl in the alkylamino for $Rc^4$ are linear or branched alkyls having one to four carbon atoms such as methyl, ethyl, propyl, isopropyl, butyl, isobutyl, sec-butyl and tert-butyl.

In the above-mentioned general formula (5), examples of the alkyl for $Ra^5$ or $Rb^5$ are linear or branched alkyls having one to four carbon atoms such as methyl, ethyl, propyl, isopropyl, butyl, isobutyl, sec-butyl and tert-butyl. Examples of the alkyl in the alkylamino for $Rc^5$ are linear or branched alkyls having one to four carbon atoms such as methyl, ethyl, propyl, isopropyl, butyl, isobutyl, sec-butyl and tert-butyl.

In the above-mentioned general formula (6), examples of the alkyl for $Ra^6$ are linear or branched alkyls having one to four carbon atoms such as methyl, ethyl, propyl, isopropyl, butyl, isobutyl, sec-butyl and tert-butyl. Examples of the alkyl in the alkylamino for $Rc^6$ are linear or branched alkyls having one to four carbon atoms such as methyl, ethyl, propyl, isopropyl, butyl, isobutyl, sec-butyl and tert-butyl.

In the above-mentioned general formula (7), examples of the alkyl for $Ra^7$ or $Rb^7$ are linear or branched alkyls having one to four carbon atoms such as methyl, ethyl, propyl, isopropyl, butyl, isobutyl, sec-butyl and tert-butyl. Examples of the acyl in the acylamino for $Rc^7$ are linear or branched acyls having one to four carbon atoms such as formyl, acetyl, propionyl, butyryl, isobutyryl and tert-butyryl as well as benzoyl. Examples of the alkyl in the alkylamino for $Rc^7$ are linear or branched alkyls having one to four carbon atoms such as methyl, ethyl, propyl, isopropyl, butyl, isobutyl, sec-butyl and tert-butyl. Examples of the alkyl in the dialkylaminomethyleneamino group for $Rc^7$ are linear or branched alkyls having one to four carbon atoms such as methyl, ethyl, propyl, isopropyl, butyl, isobutyl, sec-butyl and tert-butyl.

In the above-mentioned general formula (8), examples of the alkyl for $Ra^8$ and $Rb^8$ are linear or branched alkyls having one to six carbon atoms such as methyl, ethyl, propyl, isopropyl, butyl, isobutyl, sec-butyl, tert-butyl, pentyl, isopentyl, neopentyl, tert-pentyl, hexyl and dimethylbutyl.

Examples of the alkyl for Xc of general formula (8) are linear or branched alkyls having one to four carbon atoms such as methyl, ethyl, propyl, isopropyl, butyl, isobutyl, sec-butyl and tert-butyl. Examples of the acyl for Xc are linear or branched acyl having one to four carbon atoms such as formyl, acetyl, propionyl, butyryl, isobutyryl and tert-butyryl.

Examples of the alkyl for Yd of general formula (8) are linear or branched alkyls having one to four carbon atoms such as methyl, ethyl, propyl, isopropyl, butyl, isobutyl, sec-butyl and tert-butyl. Examples of the halogen for Yd are fluorine, chlorine, bromine and iodine. Examples of the alkoxycarbonyl for Yd are carbonyls to which a linear or branched alkoxy group having one to four carbon atoms such as methoxy, ethoxy, propoxy, isopropoxy, butoxy, isobutoxy, sec-butoxy and tert-butoxy is bonded. Examples of the alkoxysulfonyl group for Yd are sulfonyls to which the same linear or branched alkoxy having one to four carbon atoms as above are bonded. Examples of the alkyl in the dialkylaminosulfonyl group for Yd are linear or branched alkyls having one to four carbon atoms such as methyl, ethyl, propyl, isopropyl, butyl, isobutyl, sec-butyl and tert-butyl.

Preferred compounds of the present invention are:
1,3-Dimethylpyrido[2,3-d]pyrimidine-2,4-dione (Compound 1)
5-Amino-1,3-dimethylpyrido[2,3-d]pyrimidine-2,4-dione (Compound 2)
5-Amino-1,3-diethylpyrido[2,3-d]pyrimidine-2,4-dione (Compound 3)
5-Amino-1-isobutyl-3-methylpyrido[2,3-d]pyrimidine-2,4-dione (Compound 4)
1,3-Dimethyl-5-methylaminopyrido[2,3-d]pyrimidine-2,4-dione (Compound 5)
1,3-Diethyl-5-methylaminopyrido[2,3-d]pyrimidine-2,4-dione (Compound 6)
5-Allylamino-1,3-dimethylpyrido[2,3-d]pyrimidine-2,4-dione (Compound 7)
1,3-Dimethyl-5-isopropylaminopyrido[2,3-d]pyrimidine-2,4-dione (Compound 8)
1,3-Dimethyl-5-hydroxyaminopyrido[2,3-d]pyrimidine-2,4-dione (Compound 9)

1,3-Dimethyl-5-hydrazinopyrido[2,3-d]pyrimidine-2,4-dione (Compound 10)

1,3-Dimethyl-5-(2-hydroxyethyl)aminopyrido[2,3-d]pyrimidine-2,4-dione (Compound 11)

1,3-Dimethyl-5-hydroxypyrido[2,3-d]pyrimidine-2,4-dione (Compound 12)

7-Amino-1,3-dimethylpyrido[2,3-d]pyrimidine-2,4-dione (Compound 13)

6-Amino-1,3-dimethylpyrido[2,3-d]pyrimidine-2,4-dione (Compound 14)

7-Amino-1,3-dimethyl-5-hydroxypyrido[2,3-d]pyrimidine-2,4-dione (Compound 15)

1,3-Dimethyl-5-tert-butylaminopyrido[2,3-d]pyrimidine-2,4-dione (Compound 16)

7-Amino-1-isobutyl-3-methylpyrido[2,3-d]pyrimidine-2,4-dione (Compound 17)

5-Amino-1,3-diethyl-6-methylpyrido[2,3-d]pyrimidine-2,4-dione (Compound 18)

5-Amino-1,3-diethyl-6-fluoropyrido[2,3-d]pyrimidine-2,4-dione (Compound 19)

5-Amino-6-bromo-1,3-diethylpyrido[2,3-d]pyrimidine-2,4-dione (Compound 20)

5-Amino-1,3-diethyl-6-hydroxypyrido[2,3-d]pyrimidine-2,4-dione (Compound 21)

1,3-Diethyl-5-isopropylamino-6-methylpyrido[2,3-d]pyrimidine-2,4-dione (Compound 22)

1,3-Diethyl-5-dimethylaminomethyleneamino-6-methylpyrido-[2,3-d]pyrimidine-2,4-dione (Compound 23)

5-Acetylamino-1,3-diethyl-6-methylpyrido[2,3-d]pyrimidine-2,4-dione (Compound 24)

5-Benzylamino-1,3-diethylpyrido[2,3-d]pyrimidine-2,4-dione (Compound 25)

1,3-Diethyl-5-isopropylaminopyrido[2,3-d]pyrimidine-2,4-dione (Compound 26)

5-Amino-1,3-diethyl-7-methylpyrido[2,3-d]pyrimidine-2,4-dione (Compound 27)

1,3-Diethyl-5-isopropylamino-7-methylpyrido[2,3-d]pyrimidine-2,4-dione (Compound 28)

5-Aminopyrido[2,3-d]pyrimidine-2,4-dione (Compound 29)

5-Amino-3-methylpyrido[2,3-d]pyrimidine-2,4-dione (Compound 30)

5-Amino-3-ethylpyrido[2,3-d]pyrimidine-2,4-dione (Compound 31)

5-Amino-1-methylpyrido[2,3-d]pyrimidine-2,4-dione (Compound 32)

5-Amino-1-ethylpyrido[2,3-d]pyrimidine-2,4-dione (Compound 33)

5-Amino-3-ethyl-1-methylpyrido[2,3-d]pyrimidine-2,4-dione (Compound 34)

5-Amino-1-ethyl-3-methylpyrido[2,3-d]pyrimidine-2,4-dione (Compound 35)

5-Amino-1-benzylpyrido[2,3-d]pyrimidine-2,4-dione (Compound 36)

5-Amino-1-benzyl-3-methylpyrido[2,3-d]pyrimidine-2,4-dione (Compound 37)

5-Amino-1-benzyl-3-ethylpyrido[2,3-d]pyrimidine-2,4-dione (Compound 38)

5-Isopropylaminopyrido[2,3-d]pyrimidine-2,4-dione (Compound 39)

5-Isopropylamino-3-methylpyrido[2,3-d]pyrimidine-2,4-dione (Compound 40)

3-Ethyl-5-isopropylaminopyrido[2,3-d]pyrimidine-2,4-dione (Compound 41)

5-Isopropylamino-1-methylpyrido[2,3-d]pyrimidine-2,4-dione (Compound 42)

1-Ethyl-5-isopropylaminopyrido[2,3-d]pyrimidine-2,4-dione (Compound 43)

3-Ethyl-5-isopropylamino-1-methylpyrido[2,3-d]pyrimidine-2,4-dione (Compound 44)

1-Ethyl-5-isopropylamino-3-methylpyrido[2,3-d]pyrimidine-2,4-dione (Compound 45)

1-Benzyl-5-isopropylaminopyrido[2,3-d]pyrimidine-2,4-dione (Compound 46)

1-Benzyl-5-isopropylamino-3-methylpyrido[2,3-d]pyrimidine-2,4-dione (Compound 47)

1-Benzyl-3-ethyl-5-isopropylaminopyrido[2,3-d]pyrimidine-2,4-dione (Compound 48)

5-Benzylaminopyrido[2,3-d]pyrimidine-2,4-dione (Compound 49)

1-Benzyl-5-benzylaminopyrido[2,3-d]pyrimidine-2,4-dione (Compound 50)

5-Acetylamino-1,3-dimethylpyrido[2,3-d]pyrimidine-2,4-dione (Compound 51)

5-Benzoylamino-1,3-dimethylpyrido[2,3-d]pyrimidine-2,4-dione (Compound 52)

1,3-Dimethyl-5-dimethylaminomethyleneaminopyrido[2,3-d]pyrimidine-2,4-dione (Compound 53)

5-Acetylamino-1,3-diethylpyrido[2,3-d]pyrimidine-2,4-dione (Compound 54)

5-Benzoylamino-1,3-diethylpyrido[2,3-d]pyrimidine-2,4-dione (Compound 55)

1,3-Diethyl-5-dimethylaminomethyleneaminopyrido[2,3-d]-pyrimidine-2,4-dione (Compound 56)

5-Amino-6-benzyloxy-1,3-diethylpyrido[2,3-d]pyrimidine-2,4-dione (Compound 57)

5-Amino-6-cyano-1,3-diethylpyrido[2,3-d]pyrimidine-2,4-dione (Compound 58)

5-Amino-1,3-diethyl-6-ethoxycarbonylpyrido[2,3-d]pyrimidine-2,4-dione (Compound 59)

5-Amino-6-carboxy-1,3-diethylpyrido[2,3-d]pyrimidine-2,4-dione (Compound 60)

5-Amino-1,3-diethyl-6-methoxysulfonylpyrido[2,3-d]pyrimidine-2,4-dione (Compound 61)

5-Amino-6-aminosulfonyl-1,3-diethylpyrido[2,3-d]pyrimidine-2,4-dione (Compound 62)

5-Amino-1,3-diethyl-6-diethylaminosulfonylpyrido[2,3-d]-pyrimidine-2,4-dione (Compound 63)

5-Amino-1,3-diethyl-6-sulfopyrido[2,3-d]pyrimidine-2,4-dione (Compound 64)

5-Amino-1,3-diethyl-6-nitropyrido[2,3-d]pyrimidine-2,4-dione (Compound 65)

5,6-Diamino-1,3-diethylpyrido[2,3-d]pyrimidine-2,4-dione (Compound 66)

7-Amino-1,3-diethylpyrido[2,3-d]pyrimidine-2,4-dione (Compound 67)

7-Amino-1,3-diethyl-6-ethoxycarbonylpyrido[2,3-d]pyrimidine-2,4-dione (Compound 68)

1,3-Diethyl-5-formamidopyrido[2,3-d]pyrimidine-2,4-dione (Compound 69)

1,3-Diethyl-5-formamido-6-methylpyrido[2,3-d]pyrimidine-2,4-dione (Compound 70)

The pyrido[2,3-d]pyrimidine derivatives according to the present invention include the pharmaceutically-acceptable salts of the compounds represented by the above-given general formulas (A) and (1) through (8) such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, sulfanilic acid, salts with alkali metals such as sodium or potassium, salts with alkaline-earth metals such as calcium or magnesium, or salts with other metals such as aluminum. The pyrido[2,3-d]pyrimidine derivatives of the invention may also include metal complexes of the compounds represented by formulas (A) and (1) through (8). For example, the derivatives include complexes with zinc, nickel, cobalt, copper, iron, etc. The salts and metal complexes may be manufactured from the pyrido[2,3-d]pyrimidine compounds or derivatives of the present invention in a free state or may be mutually converted from one to another by conventional means.

When the compounds of the present invention have stereoisomers such as cis-trans isomers, optical isomers, conformational isomers, etc. or exist in a form of hydrates, the present invention includes any of such stereoisomers and hydrates.

The compounds of the present invention may be manufactured by methods described in Laid-Open Japanese Patent Publication Sho-63/45279 and corresponding U.S. Pat. No. 4,808,587, or by a method similar thereto, said Japanese patent publication and said U.S. Pat. No. 4,808,587 being incorporated herein by reference in their entireties. For example, as disclosed in U.S. Pat. No. 4,808,587, pyrido[2,3-d]pyrimidine derivatives may be prepared using uracil derivatives as a starting material, or by subjecting pyrido[2,3-d]pyrimidine derivatives obtained thereby to further reactions such as catalytic reduction, halogenation, and the like. See U.S. Pat. No. 4,808,587, col. 1 line 38 to col. 2 line 4, and col. 2 line 68 to col. 4 line 30, herein incorporated by reference. In addition, with respect to novel substances, the manufacturing method is described in more detail in the following examples wherein all parts, percentages, ratios, and amounts are by weight, and all temperatures are in °C. unless otherwise indicated:

EXAMPLE 1

(1) 1-Benzyl-5-chloropyrido[2,3-d]pyrimidine-2,4-dione (3 g) and 1 g sodium azide were dissolved in 30 ml of dimethyl formamide (DMF) and stirred at room temperature for 10 hours. The reaction solution was added to 400 ml of water, the separated crystals were filtered, dried, dissolved in 150 ml of methanol, 0.5 g of 10% palladium-carbon was added and the mixture was stirred in a hydrogen atmosphere at room temperature for 15 hours. The catalyst was removed, the filtrate was concentrated, the residue was dissolved in 1N hydrochloric acid, the solution was washed with chloroform and the aqueous layer was neutralized with 20% sodium hydroxide. The separated crystals were extracted with chloroform, the organic layer was concentrated and the resulting crystals were recrystallized from ethyl acetate to give 1.5 g of the compound 36.

Melting point: 291.5°–292° C. NMR(DMSO-$d_6$): 5.30(s, 2H), 6.40(d,1H), 7.16–7.32(m,5H), 7.62(bs,1H), 7.90(d, 1H), 8.19(bs,1H), 11.45(bs,1H)

1-Substituted, 3-substituted or 1,3-disubstituted-5-chloropyrido[2,3-d]pyrimidine-2,4-diones were treated similarly to the treatment of the 1-benzyl substituted reactant to give the following compounds:

(Compound 32)

Melting point: >300° C. NMR(DMSO-$d_6$): 3.38(s,3H), 6.39(d,1H), 7.58(bs,1H), 7.94(d,1H), 8.16(bs,1H), 11.33(bs,2H)

(Compound 33)

Melting point: >300° C. NMR(DMSO-$d_6$): 1.13(t,3H), 4.12(q,2H), 6.39(d,1H), 7.57(bs,1H), 7.95(d,1H), 8.17(bs,1H), 11.32(bs,1H)

(Compound 34)

Melting point: 211°–212° C. NMR(DMSO-$d_6$): 1.14(t,3H), 3.46(s,3H), 3.91(q,2H), 6.42(d,1H), 7.62(bs,1H), 7.95(d,1H), 8.26(bs,1H)

(Compound 35)

Melting point: 246°–247° C. NMR(DMSO-$d_6$): 1.16(t,3H), 3.24(s,3H), 4.20(q,2H), 6.42(d,1H), 7.60(bs,1H), 7.96(d,1H), 8.25(bs,1H)

(Compound 37)

Melting point: 187°–188° C. NMR(DMSO-$d_6$): 3.26(s,3H), 5.37(s,2H), 6.44(d,1H), 7.16–7.33(m,5H), 7.66(bs,1H), 7.92(d,1H), 8.23(bs,$_1$H)

(Compound 38)

Melting point: 187°–188° C. NMR(DMSO-$d_6$): 1.15(t,3H), 3.93(q,2H), 5.37(s,2H), 6.45(d,1H), 7.16–7.3(m,5H), 7.68(bs,1H), 7.90(d,1H), 8.29(bs,1H)

(2) 5-Chloro-1,3-diethylpyrido[2,3-d]pyrimidine-2,4-dione (5 g) and 3.5 g of isopropylamine were dissolved in 70 ml of DMF and stirred at room temperature for 12 hours. The reaction solution was added to ice water and the separated crystals were filtered, dried and purified by a column of silica gel to give 4.9 g of the compound 26.

Melting point: 118°–119° C. NMR(DMSO-$d_6$): 1.12(t,3H), 1.18(t,3H), 1.22(d,6H), 3.75–3.88(m,1H), 3.85(q,2H), 4.21(q,2H), 6.41(d,1H), 7.96(d,1H), 8.91(d,$_1$H), 11.47(bs,1H)

1-Substituted, 3-substituted or 1,3-disubstituted-5-chloropyrido[2,3-d]pyrimidine-2,4-diones were similarly reacted with various substituted amines to give the following compounds:

(Compound 25)

Melting point: 111°–112° C. NMR(DMSO-$d_6$): 1.15(t,3H), 1.17(t,3H), 3.93(q,2H), 4.21(q,2H), 4.56(d,2H), 6.45(d,1H), 7.2–7.4(m,5H), 8.05(d,1H), 9.57(t,1H)

(Compound 42)

Melting point: 215.8°–216.6° C. NMR(DMSO-$d_6$): 1.22(d,6H), 3.39(s,3H), 3.81(dq,1H), 6.48(d,1H), 8.06(d,1H), 8.99(d,1H), 11.45(bs,1H)

(Compound 43)

Melting point: 227°–228° C. NMR(DMSO-$d_6$): 1.14(t,3H), 1.21(d,6H), 3.82(dq,1H), 4.13(q,2H), 6.48(d,1H), 8.07(d,1H), 9.00(d,1H), 11.43(bs,1H)

(Compound 44)

Melting point: 141.0°–141.5° C. NMR(DMSO-$d_6$): 1.14(t,3H), 1.23(d,6H), 3.47(s,3H), 3.84(dq,1H), 3.92(q,2H), 6.52(d,1H), 8.08(d,1H), 9.10(d,1H)

(Compound 45)

Melting point: 95°–96.5° C. NMR(DMSO-$d_6$): 1.16(t,3H), 1.23(d,6H), 3.24(s,3H), 3.84(dq,1H), 4.21(q,2H), 6.51(d,1H), 8.08(d,1H), 9.10(d,1H)

(Compound 46)

Melting point: 205°–206° C. NMR(DMSO-$d_6$): 1.22(d,6H), 3.82(m,1H), 5.31(s,2H), 6.49(d,1H), 7.16–7.33(m,5H), 8.02(d,1H), 9.01(d,1H), 11.56(bs,1H)

(Compound 47)

Melting point: 128°–129° C. NMR(DMSO-$d_6$): 1.23(d,6H), 3.26(s,3H), 3.84(dq,1H), 5.39(s,2H), 6.52(d,1H), 7.15–7.33(m,5H), 8.04(d,1H), 9.12(d,1H)

(Compound 48)

Melting point: 136°–137° C. NMR(DMSO-$d_6$): 1.15(t,3H), 1.23(d,6H), 3.84(dq,1H), 3.94(q,2H), 5.39(s,2H), 6.52(d,1H), 7.15–7.3(m,5H), 8.03(d,1H), 9.13(d,1H)

(Compound 50)

Melting point: 223.4°–224.6° C. NMR(DMSO-$d_6$): 4.57(d,2H), 5.31(s,2H), 6.44(d,1H), 7.16–7.42(m,10H), 7.99(d,1H), 9.49(t,1H), 11.59(bs,1H)

(Compound 51)
Melting point: 196°–197° C.
(Compound 52)
Melting point: 243°–244° C.
(Compound 53)
Melting point: 149°–150° C.
(Compound 54)
Melting point: 141°–142° C.
(Compound 55)
Melting point: 191°–192° C.
(Compound 56)
Melting point: 100°–101° C.
(Compound 69)
Melting point: 163°–164° C.

EXAMPLE 2

The compound 46 (7.5 g) and 1 g of 10% palladium-carbon were added to 600 ml of acetic acid and stirred at 50° C. for 15 hours. Active carbon was added to the reaction solution, heated to reflux for 30 hours, the insoluble matters were filtered off and the filtrate was concentrated. Ethanol was added to the residue and the crystals were collected by filtration followed by drying to give 5 g of the compound 39.

Melting point: >300° C. NMR(DMSO-$d_6$): 1.21(d,6H), 3.78(dq,1H), 6.39(d,1H), 7.94(d,1H), 8.79(d,1H), 11.18(bs, 2H)

The compounds 36, 37, 38, 47, 48 and 50 were similarly treated to give the following compounds:
(Compound 29)

Melting point: >300° C. NMR(DMSO-$d_6$): 6.30(d,1H), 7.50(bs,1H), 7.84(d,1H), 8.01(bs,1H), 11.69(bs,2H)
(Compound 30)

Melting point: >300° C. NMR(DMSO-$d_6$): 3.17(s,3H), 6.34(d,1H), 7.55(bs,1H), 7.83(d,1H), 8.09(bs,1H)
(Compound 31)

Melting point: >300° C. NMR(DMSO-$d_6$): 1.11(t,3H), 3.85(q,2H), 6.33(d,1H), 7.55(bs,1H), 7.83(d,1H), 8.10(bs, 1H), 11.38(bs,1H)
(Compound 40)

Melting point: 240.5°–241° C. NMR(DMSO-$d_6$): 1.22(d, 6H), 3.17(s,3H), 3.81(dq,1H), 6.41(d,1H), 7.96(d,1H), 8.90 (d,1H), 11.48(bs,1H)
(Compound 41)

Melting point: 249.5°–250° C. NMR(DMSO-$d_6$): 1.16(t, 3H), 1.22(d,6H), 3.8(dq,1H), 3.85(q,2H), 6.41(d,$_1$H), 7.96 (d,1H), 8.9(d,1H)
(Compound 49)

Melting point: >300° C. NMR(DMSO-$d_6$): 4.54(d,2H), 6.34(d,1H), 7.22–7.42(m,5H), 7.92(d,1H), 9.27(t,1H), 11.21 (bs,1H), 11.25(bs,1H)

EXAMPLE 3

(1) 5-Chloro-1,3-diethyl-6-methylpyrido[2,3-d]pyrimidine-2,4-dione was used instead of 1-benzyl-5-chloropyrido[2,3-d]pyrimidine-2,4-dione in the above-mentioned Example 1 (1) and the same reaction as in Example 1 (1) was carried out to give the compound 18.

Melting point: 178°–180° C. NMR(DMSO-$d_6$): 1.14(t, 3H), 1.15(t,3H), 2.03(s,3H), 3.93(q,2H), 4.19(q,2H), 7.0(bs, 1H), 7.91(s,1H), 8.67(bs,1H)

(2) 5-Chloro-1,3-diethyl-6-methylpyrido[2,3-d]pyrimidine-2,4-done was used instead of 5-chloro-1,3-diethylpyrido[2,3-d]pyrimidine-2,4-dione in the above-mentioned Example 1 (2) and the same reaction as in Example 1 (2) was carried out to give the compound 22.

Melting point: 119.5°–120.0° C. NMR(DMSO-$d_6$): 1.14 (t,3H), 1.16(t,3H), 1.20(d,6H), 2.29(s,3H), 3.93(q,2H), 4.19 (q,2H), 4.2(dq,1H), 7.94(s,1H), 9.71(d,1H)

EXAMPLE 4

The compound 3 (2.3 g) was dissolved in 60 ml of tetrachloromethane, then 0.76 ml of pyridine and 1.6 g of bromine were added thereto and the mixture was heated to reflux for 1.5 hours. The reaction solution was concentrated and water was added to the residue followed by filtering to collect the crystals. They were washed with water and recrystallized from ethanol to give 30 g of the compound 20.

Melting point: 154°–155° C. NMR(DMSO-$d_6$): 1.15(t, 3H), 1.18(t,3H), 3.93(q,2H), 4.17(q,2H), 7.18(bs,1H), 8.31 (s,1H), 8.94(bs,1H)

EXAMPLE 5

(1) The compound 18 (3 g) was dissolved in 10 ml of DMF, then 8.3 ml of dimethylformamide dimethylacetal were added thereto and the mixture was heated at 110° C. with stirring overnight. The reaction solution was concentrated, hexane was added to the residue and the resulting crystals were filtered and recrystallized from hexane to give 2.8 g of the compound 23. The compound 23 was further treated with a column of silica gel and recrystallized from a mixed solvent of petroleum ether and benzene to give the compound 70.
(Compound 23)

Melting point: 174°–175° C. NMR(DMSO-$d_6$): 1.10(t, 3H), 1.18(t,3H), 2.05(s,3H), 3.01(s,6H), 3.89(q,2H), 4.25(q, 2H), 7.40(s,1H), 8.19(s,1H)
(Compound 70)

Melting point: 142°–143° C.

(2) The compound 18 (2 g) was added to 20 ml of acetic anhydride and heated to reflux overnight. After it was well allowed to cool, the separated crystals were added to ether and the mixture was filtered followed by recrystallizing from ethanol to give 1.6 g of the compound 24.

Melting point: 157°–158° C. NMR(DMSO-$d_6$): 1.12(t, 3H), 1.25(t,3H), 2.14(s,3H), 2.20(s,3H), 3.91(q,2H), 4.30(q, 2H), 8.79(s,1H)

EXAMPLE 6

(1) 1,3-Diethyl-7-methyl-5-(p-toluenesulfonyloxy)pyrido [2,3-d]pyrimidine-2,4-dione was used instead of 1-benzyl-5-chloropyrido[2,3-d]pyrimidine-2,4-dione in the above-mentioned Example 1 (1) and the same reaction as in Example 1 (1) was carried out to give the compound 27.

Melting point: 198.5°–199.0° C. NMR(DMSO-$d_6$): 1.13 (t,3H), 1.16(t,3H), 2.27(s,3H), 3.91(q,2H), 4.19(q,2H), 6.28 (s,1H), 7.48(bs,1H), 8.16(bs,1H)

(2) 1,3-Diethyl-7-methyl-5-(p-toluenesulfonyloxy)pyrido [2,3-d]pyrimidine-2,4-dione was used instead of 5-chloro-1,3-diethylpyrido[2,3-d]pyrimidine-2,4-dione in the above-mentioned Example 1 (2) and the same reaction as in Example 1 (2) was carried out to give the compound 28.
(Compound 28)

Melting point: 92°–93° C. NMR(DMSO-$d_6$): 1.13(t,3H), 1.16(t,3H), 1.22(d,6H), 2.34(s,3H), 3.82(dq,1H), 3.91(q, 2H), 4.20(q,2H), 6.40(s,1H), 8.99(d,1H)

EXAMPLE 7

5-Chloro-1,3-diethyl-6-fluoropyrido[2,3-d]pyrimidine-2,4-dione (6.2 g) and 50 ml of 28% ammonium hydroxide were heated at 150° C. for 2 hours in a simple polymerizing device. After cooling, the mixture was extracted with chloroform, the extract was dried with sodium sulfate and the solvent was evaporated therefrom. The resulting crystals were recrystallized from ethanol to give 4.5 g of the compound 19.

Melting point: 201°–202° C. NMR(DMSO-$d_6$): 1.15(t, 3H), 1.16(t,3H), 3.92(q,2H), 4.18(q,2H), 7.69(bs,1H), 8.17 (d,1H), 8.31(bs,1H)

5-Chloro-1,3-diethyl-6-benzyloxypyrido[2,3-d] pyrimidine-2,4-dione was treated in the same manner as the 6-fluoro substituted compound above to give the compound 57.

Melting point: 213°–215° C. NMR(DMSO-$d_6$): 1.14(t, 3H), 1.15(t,3H), 3.92(q,2H), 4.16(q,2H), 5.19(s,1H), 6.9–7.0(bs,1H), 7.3–7.6(m,5H), 7.94(s,1H), 8.3–8.4(bs,1H)

EXAMPLE 8

The compound 57 (5 g) was suspended in 300 ml of methanol and subjected to a catalytic reduction at room temperature in the presence of 500 mg of 10% palladium-carbon. When the crystals of the benzyloxy compound (the compound 57) disappeared after about 1 hour, the catalyst was filtered off and the solvent was evaporated from the filtrate. The residual crystals were recrystallized from ethanol to give 1.4 g of the compound 21.

Melting point: 213°–215° C. NMR(DMSO-$d_6$): 1.14(t, 3H), 1.15(t,3H), 3.92(q,2H), 4.16(q,2H), 6.5–7.0(bs,1H), 7.71(bs,1H), 7.9–8.3(bs,1H), 9.63(s,1H)

EXAMPLE 9

DMF (30 ml) was added to 4.2 g of potassium cyanide, 0.7 g of palladium diacetate and 3.3 g of triphenylphosphine, the mixture was stirred at room temperature for 30 minutes in an argon atmosphere and a solution of 10 g of the bromo compound (the compound 20) in 20 ml of DMF was added thereto. The reaction solution was stirred at 90° C. for 24 hours, poured into ice water and extracted with ethyl acetate. The organic layer was washed with a saturated sodium chloride solution and dried with sodium sulfate. The solvent was evaporated and the residue was purified by a column of silica gel followed by recrystallizing from benzene to give 3.5 g of the compound 58.

Melting point: 193°–195° C. NMR(DMSO-$d_6$): 1.15(t, 3H), 1.17(t,3H), 3.92(q,2H), 4.20(q,2H), 8.04(bs,1H), 8.54 (s,1H), 9.06(bs,1H)

EXAMPLE 10

(1) Raney nickel was added to an ethanolic solution of 1 g of 5-amino-1,3-diethyl-6-ethoxycarbonyl-7-methylthiopyrido[2,3-d]pyrimidine-2,4-dione and the mixture was heated to reflux for 5 hours. The catalyst was removed using celite, the filtrate was concentrated, the residue was purified by a column of silica gel and the resulting crystals were recrystallized from ethanol to give 6.0 g of the compound 59.

Melting point: 144°–145° C. NMR(DMSO-$d_6$): 1.16(t, 3H), 1.18(t,3H), 1.32(t,3H), 3.93(q,2H), 4.23(q,2H), 4.30(q, 2H), 8.49(d,1H), 7.86(s,1H), 9.36(d,1H)

(2) The compound 59 (0.56 g) was added to 10 ml of ethanol, 1 g of potassium hydroxide and 10 ml of water and the mixture was heated to reflux for 10 minutes. The reaction solution was acidified with acetic acid and the separated crystals were filtered followed by washing with water to give 0.46 g of the compound 60.

Melting point: 264°–266° C. NMR(DMSO-$d_6$): 1.16(t, 3H), 1.18(t,3H), 1.32(t,3H), 3.93(q,2H), 4.23(q,2H), 8.70(d, 1H), 8.72(s,1H), 9.28(d,1H)

EXAMPLE 11

(1) The compound 3 (1 g) was added to 3 ml of chlorosulfuric acid and stirred at 100° C. for 2 hours. The reaction solution was added to ice water and the separated crystals were filtered followed by washing with water to give 1.1 g of 5-amino-6-chlorosulfonyl-1,3-diethylpyrido[2,3-d] pyrimidine-2,4-dione.

(2) The above product (3 g) was dissolved in 30 ml of tetrahydrofuran and 20 ml of methanol, then a sodium methoxide solution prepared from 300 mg of sodium and 10 ml of methanol was added thereto and the mixture was stirred for 30 minutes. Acetic acid was added to the reaction solution to make it acidic and the solvent was evaporated therefrom. Water was added to the residue, the mixture was extracted with chloroform, the organic layer was dried with sodium sulfate, the solvent was evaporated therefrom and the residue was purified by a column of silica gel followed by recrystallizing from methanol to give 2.1 g of the compound 61.

Melting point: 156°–157° C. NMR(DMSO-$d_6$): 1.16(t, 3H), 1.20(t,3H), 3.77(s,3H), 3.93(q,2H), 4.24(q,2H), 7.28 (bs,1H), 8.55(s,1H), 9.51(bs,1H)

(3) The 6-chlorosulfonyl substituted product obtained in the above-mentioned paragraph (1) was similarly treated with ammonia, diethyl ammonium and sodium hydroxide to give the compounds 62, 63 and 64, respectively.

(Compound 62)

Melting point: 236°–238° C. NMR(DMSO-$d_6$): 1.16(t, 3H), 1.18(t,3H), 3.94(q,2H), 4.22(q,2H), 7.19(bs,1H), 7.61 (bs,2H), 8.50(s,1H), 9.41(bs,1H)

(Compound 63)

Melting point: 168°–169° C. NMR(DMSO-$d_6$): 1.07(tx2, 3Hx2), 1.15(t,3H), 1.19(t,3H), 3.25(qx2,2Hx2), 3.92(q,2H), 4.23(q,2H), 7.34(bs,1H), 8.49(s,1H), 9.39(bs,1H)

(Compound 64)

Melting point: >320° C. NMR(DMSO-$d_6$): 1.13(t,3H), 1.15(t,3H), 3.92(q,2H), 4.19(q,2H), 7.46(d,1H), 8.30(s,1H), 8.87(d,1H)

EXAMPLE 12

(1) A mixture of 40 ml of nitric acid and 40 ml of concentrated sulfuric acid was cooled with an ice bath and 10 g of the compound 3 were added. Temperature of the reaction solution was brought to room temperature, the solution was stirred for 1 hour, then stirred at 50° C. for 1 hour, added to ice water and the mixture was extracted with chloroform. The organic layer was dried with sodium sulfate, the solvent was evaporated therefrom and the resulting crystals were recrystallized from methanol to give 9.1 g of 1,3-diethyl-5-nitroaminopyrido[2,3-d]pyrimidine-2,4-dione.

(2) The above 5-nitroamino substituted product (5.3 g) was dissolved in 20 ml of sulfuric acid and stirred at 50° C. for 30 minutes. The reaction solution was added to ice water, neutralized with 28% aqueous ammonia and extracted with chloroform. The organic layer was dried with sodium sulfate, the solvent was evaporated therefrom and the resulting crude crystals were recrystallized from methanol to give 3.3 g of the product 65.

Melting point: 169°–170° C. NMR(DMSO-$d_6$): 1.17(t, 3H), 1.20(t,3H), 3.94(q,2H), 4.26(q,2H), 8.81(bs,2H), 9.15 (s,1H), 9.94(bs,1H)

(3) The compound 65 (2.9 g) was dissolved in 60 ml of ethyl acetate, 0.5 g of 10% palladium-carbon was added and the mixture was stirred at room temperature for 1 hour in a hydrogen atmosphere. The catalyst was filtered off using celite, the resulting filtrate was concentrated and the separated crystals were recrystallized from methanol to give 1.6 g of the compound 66.

Melting point: 198°–199° C. NMR(DMSO-d$_6$): 1.14(tx2, 3Hx2), 3.92(q,2H), 4.15(q,2H), 4.62(bs,1H), 7.64(s,1H), 6.5–8.5(bs,2H)

EXAMPLE 13

6-Amino-5-formyl-1,3-diethyluracil was treated by the same manner as mentioned in Example 5 of Laid-Open Japanese Patent Publication Sho-63/45279 and corresponding U.S. Pat. No. 4,808,587 to give the compound 67.

Melting point: 203°–204° C. NMR(DMSO-d$_6$): 1.13(t, 3H), 1.19(t,3H), 3.91(q,2H), 4.18(q,2H), 6.32(b,1H), 7.20 (bs,2H), 7.88(d,1H)

EXAMPLE 14

6-Amino-1,3-diethyluracil (3.0 g) and 3.4 g of ethyl 2-ethoxymethylene-2-cyanoacetate were stirred at 170° C. for 1 hour in an argon atmosphere. After cooling, methanol was added thereto, the resulting crystals were filtered and dried and the resulting mixture was purified by means of a flash column followed by recrystallizing from ethanol to give the compound 68.

Melting point: 203°–204.5° C. NMR(DMSO-d$_6$): 1.13(t, 3H), 1.20(t,3H), 1.34(t,3H), 3.89(q,2H), 4.16(q,2H), 4.29(q, 2H), 7.98(bs,1H), 8.12(bs,1H), 8.52(s,1H)

EXAMPLE 15

Now the bronchodilating action, antiallergic action, and inhibitory action against the LTD$_4$ induced bronchocontracting reaction exhibited by the pyrido[2,3-d]pyrimidine derivatives of the present invention will be described in detail as hereunder:

1. Bronchodilating Action

A guinea pig was killed by draining out the blood, the trachea was extracted out and incised along the tracheal cartilage and four tracheal slices with a width of about 1 mm were connected with a silk yarn to give a sample of tracheal smooth muscle. The sample was suspended, with a load by a tension of about 0.5 g, in a 5 ml Magnus vessel (37° C.) which was filled with a Tyrode solution tissue culture media and aerated with a mixture of 95% oxygen and 5% carbon dioxide. When the base line became stable after allowing to stand for 0.5–1 hour, histamine dihydrochloride was made to act therewith and the resulting isotonic contraction was recorded through an isotonic transducer.

Investigation of the bronchodilating action of the test compounds was conducted using a relaxing action to the sustained contracting reaction by the contracting agent as an index. Thus, after the sustained contracting reaction of the smooth muscle by $10^{-4}$M histamine dihydrochloride became constant, the test compound was made to act therewith at the concentration of $10^{-5}$M, the relaxation rate to the sustained contracting height was calculated and the activity was evaluated in terms of the strength of said relaxation rate. The length of tracheal smooth muscle relaxed by the test compound divided by the sustained length contracted by histamine dihydrochloride is called the relaxation rate.

An example of the results of the experiments is given in Table 1:

TABLE 1

| Bronchodilating Action As Measured By Relaxation Rate (%) | |
|---|---|
| Compound No. | Relaxation Rate (%) |
| 2 | 33.3 |
| 3 | 130.8 |
| 4 | 85.7 |
| 6 | 83.8 |
| 17 | 100.0 |
| 18 | 110.8 |
| 19 | 96.2 |
| 20 | 103.4 |
| 21 | 99.0 |
| 22 | 134.4 |
| 24 | 20.6 |
| 25 | 100.0 |
| 26 | 29.2 |
| 27 | 84.3 |
| 28 | 148.0 |
| 29 | 12.5 |
| 30 | 12.2 |
| 31 | 21.2 |
| 32 | 25.7 |
| 33 | 47.9 |
| 34 | 72.9 |
| 35 | 107.9 |
| 36 | 18.2 |
| 37 | 48.1 |
| 38 | 93.0 |
| 39 | 100.0 |
| 40 | 60.0 |
| 41 | 65.8 |
| 42 | 73.3 |
| 43 | 72.9 |
| 44 | 104.2 |
| 45 | 53.2 |
| 46 | 46.5 |
| 47 | 29.8 |
| 48 | 13.8 |
| 51 | 18.2 |
| 53 | 25.0 |
| 54 | 82.8 |
| 55 | 38.3 |
| 56 | 93.3 |
| 57 | 93.8 |
| 58 | 115.9 |
| 59 | 35.4 |
| 60 | 18.3 |
| 61 | 62.1 |
| 62 | 43.4 |
| 63 | 67.9 |
| 65 | 100.0 |
| 66 | 90.3 |
| 67 | 98.4 |
| 68 | 27.1 |
| 69 | 96.2 |
| 70 | 117.6 |

2. Antiallergic Action

Antiallergic action of the compounds of the present invention was evaluated by means of a passive cutaneous anaphylaxis (PCA) in rats.

A passive sensitization was conducted by a subcutaneous administration of a solution of anti-DNP-Asc (2,4-dinitrophenyl ascaris) diluted with a physiological saline solution to four places of the back of a group of six male rats of the Wister strain (six weeks age) whose backs were shaved. Thus, after one hour from the oral administration of the test compound, a mixture of equal amounts of DNP-Asc solution (5 mg/ml) and 2% Evans blue solution was intravenously administered to induce a PCA reaction. After 30 minutes, the rats were killed by decapitating and draining out the blood. The parts having blue spots were cut out and the amount of the leaked dye was measured. Thus, the skin was dissolved by 2N aqueous solution of potassium hydroxide, centrifuged after adding 2N aqueous solution of phosphoric acid and acetone and the amount of the dye was measured from the absorbance at 620 nm of the resulting supernatant liquid whereby the inhibiting rate against the dye leakage was determined.

As a result, a significant inhibitory action against the dye leakage was observed in a group where 20 mg/kg of the compounds of the present invention were orally administered as compared with the control.

3. Inhibitory Action Against the Bronchocontracting Reaction Induced by LTD4

The inhibitory action of the compounds of the present invention against the bronchocontracting reaction induced by $LTD_4$ was measured according to a modified Konzett and Rossler's method using Hartley male guinea pigs [cf. Japan. J. Pharmacol., vol.30, 537 (1980)].

As a result, an inhibitory action which was as strong as that after 1 hour from the administration was observed in the case of the compounds of the present invention represented by the general formula (8) even after 5 hours from the administration of the compounds to the induction of a bronchocontracting reaction in guinea pigs by $LTD_4$. On the contrary, in the case of the known compounds having no substituent at the 7-position of the present invention compound, the inhibitory action against the bronchial contraction was hardly noted after 5 hours from their administration. It is believed that the effect of elongating the duration of the inhibitory action is due to the structural character of the compound of the present invention that they have a substituent at the 7-position of the structure represented by the general formula (8).

It is clear from the results of the above-mentioned pharmacological experiments that the pyrido[2,3-d]pyrimidine derivatives of the present invention exhibit an excellent bronchodilating action. The pyrido[2,3-d]pyrimidine derivatives which are disclosed in Japanese Laid-Open Patent Publication Sho-63/45279 and corresponding U.S. Pat. No. 4,808,587 exhibit an antiallergic action as mentioned already. However, although such an action is able to prevent the onset of asthma symptoms involving the chemical mediators such as histamine, it is not capable of dilating the contracted bronchus and of remedying the laboring breath of asthma. Thus, the present invention offers a rapid-acting agent which directly acts on the contracted tracheal smooth muscle to make it relaxed so that the symptoms of laboring breath upon the onset of asthma can be relieved. The agent of the present invention is highly useful as a bronchodilator which can be used as a remedy not only for allergic asthma but also for various types of bronchial asthma such as endogenous asthma, exogenous asthma and dust asthma.

The pyrido[2,3-d]pyrimidine derivatives represented by the general formulae (1) to (8) are novel substances and they exhibit both excellent bronchodilating and antiallergic actions. They are quite useful as agents for treating various allergic diseases such as allergic rhinitis, allergic conjunctivitis, urticaria, allergic skin diseases, etc. as well as for bronchial asthma. In addition, the compounds represented by the general formula (8) have a characteristic feature that duration of their action is long. They are advantageously used as pharmaceuticals because their administering frequency per day or their dose can be reduced as a result of their long-lasting effectiveness.

The compounds of the present invention can be made into pharmaceutical preparations by combining the compounds with a suitable pharmaceutical carrier or diluent. They can be made into various types of preparations by conventional methods to obtain solid, semisolid, liquid or aerosol formulations for administration by oral or parenteral means.

In preparing the preparations, the compounds of the present invention may be used in the form of their pharmaceutically acceptable salts or metal complexes. The compounds may also be used either solely or jointly together in pharmaceutically effective amounts with pharmaceutically effective amounts of other pharmaceutically-active components for treating animals or humans.

In the case of preparations for oral administration, the compound of the present invention per se or a mixture of it with conventional excipients such as a suitable additive (e.g. lactose, mannitol, corn starch, potato starch, or other fillers) may be mixed with: (1) binders such as crystalline cellulose, cellulose derivatives, gum arabicum, corn starch, gelatin, etc., (2) disintegrating agents such as corn starch, potato starch, potassium carboxymethylcellulose, etc., (3) lubricating agents such as talc, magnesium stearate, etc. and (4) other pharmaceutically acceptable ingredients including bulking agents, moisturizing agents, buffers, preservatives, perfumes and the like to give tablets, diluted powders, granules or capsules.

In the case of injections, it is possible to prepare solutions or suspensions of the compounds of the invention in aqueous and nonaqueous pharmaceutically acceptable solvents such as distilled water for injection, physiological saline solution, Ringer's solution, plant oil, synthetic fatty acid glycerides, higher fatty acid esters, propylene glycol, etc.

Depending upon the state of the patient and the type of the disease, other pharmaceutical preparations may be prepared which are appropriate for the treatment or therapy. Exemplary of other preparations which may be prepared with the compounds of the present invention are inhalating agents, aerosol agents, suppositories, ointments, poultices, eye drops, etc.

The preferred dose of the compound of the present invention may vary depending upon the object to be administered, form of the preparation, method for the administration, term for the administration, etc. To achieve a desired effect, 1–1,000 mg per day, preferably 5–500 mg per day may be usually given to average adults by the oral route at one time or in a divided manner for several times a day.

In the case of a parenteral administration such as by injection, it is preferred that, due to the influence of absorption, etc., a level of from ⅓ to ¹/₁₀ of the above-given oral dose is administered parenterally.

Examples of pharmaceutical formulations containing the compounds of the present invention as an effective component are given in Tables 2, 3 and 4:

TABLE 2

Tablet Formulation

| Components | Amount per Tablet |
|---|---|
| Compound of this Invention | 20 mg |
| Lactose | 130 mg |
| Crystalline cellulose | 40 mg |
| Magnesium stearate | 10 mg |
| Total | 200 mg |

TABLE 3

Injection Formulation

| Components | Amount per Ampoule |
| --- | --- |
| Compound of the Invention | 5 mg |
| Sodium chloride | q.s. |
| Distilled water for injection | q.s. |
| Total | 1 ml |

TABLE 4

Inhalating Agent Formulation

| Components | Amount per Inhalation |
| --- | --- |
| Compound of the Invention | 1 g |
| Lactose | 5 g |
| Total | 6 g |

We claim:

1. A method of dilating the contracted bronchus and of remedying the laboring breath of bronchial asthma comprising administering to a patient having a contracted bronchus a pharmaceutically effective amount of at least one of the pyrido[2,3-d]pyrimidine derivatives represented by the general formula (A) or pharmaceutically acceptable salts or metal complexes of the compounds of formula (A) which directly acts on the contracted tracheal smooth muscle to relax it and remedy the laboring breath of bronchial asthma:

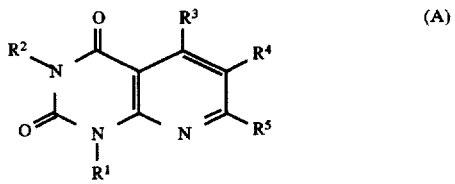

wherein $R^1$ and $R^2$ may be the same or different and each of $R^1$ and $R^2$ is hydrogen, alkyl or benzyl; $R^3$ is isopropylamino; $R^4$ is hydrogen, alkyl, halogen, nitro, amino, hydroxyl, benzyloxy, cyano, carboxyl, alkoxycarbonyl, alkoxysulfonyl, aminosulfonyl, dialkylaminosulfonyl or sulfo; and $R^5$ is hydrogen, alkyl or amino; with the proviso that only one of $R^4$ and $R^5$ may be hydrogen.

2. A method as claimed in claim 1 wherein the administration is by inhalation.

3. A compound represented by the general formula (1) or a pharmaceutically acceptable salt or metal complex thereof:

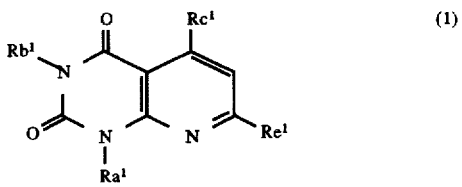

wherein $Ra^1$ and $Rb^1$ are the same or different and each of $Ra^1$ and $Rb^1$ is alkyl; $Rc^1$ is isopropylamino or amino and $Re^1$ is alkyl.

4. A method of dilating the contracted bronchus and of remedying the laboring breath of bronchial asthma comprising administering to a patient having a contracted bronchus a pharmaceutically effective amount of at least one compound represented by the general formula (8) or salt of the compounds of formula (8) which directly acts on the contracted tracheal smooth muscle to relax it and remedy the laboring breath of bronchial asthma:

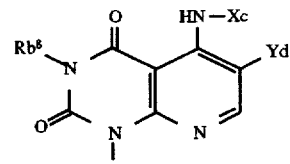

wherein $Ra^8$ and $Rb^8$ are the same or different and each of $Ra^8$ and $Rb^8$ is alkyl; Xc is hydrogen, alkyl or acyl; and Yd is alkyl halogen, nitro, amino, hydroxyl, benzyloxy, cyano, carboxyl, alkoxycarbonyl, alkoxysulfonyl, aminosulfonyl, dialkylaminosulfonyl or sulfo.

5. A compound represented by the general formula (3) or a pharmaceutically acceptable salt or metal complex thereof:

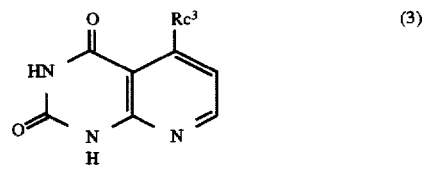

wherein $Rc^3$ is isopropylamino or benzylamino.

6. A compound represented by the general formula (4) or a pharmaceutically acceptable salt or metal complex thereof:

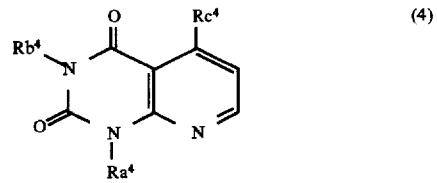

wherein one of $Ra^4$ and $Rb^4$ is hydrogen and the other is alkyl; and $Rc^4$ is isopropylamino.

7. A method of dilating the contracted bronchus and of remedying the laboring breath of bronchial asthma comprising administering to a patient having a contracted bronchus a pharmaceutically effective amount of at least one of the pyrido[2,3-d]pyrimidine derivatives represented by the general formula (A) or pharmaceutically acceptable salts or metal complexes of the compounds of formula (A) which directly acts on the contracted tracheal smooth muscle to relax it and remedy the laboring breath of bronchial asthma:

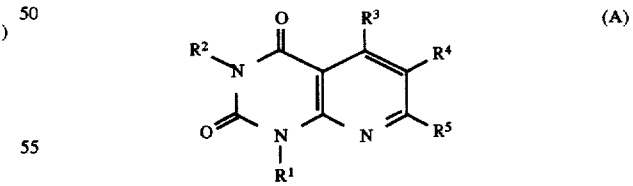

wherein $R^1$ and $R^2$ may be the same or different and each of $R^1$ and $R^2$ is hydrogen, alkyl or benzyl; $R^3$ is hydroxyl, dialkylaminomethyleneamino or —NH—X; X is hydrogen, alkyl, alkenyl, hydroxyl, amino, hydroxyalkyl, benzyl or acyl; $R^4$ is alkyl, halogen, nitro, amino, hydroxyl, benzyloxy, cyano, carboxyl, alkoxycarbonyl, alkoxysulfonyl, aminosulfonyl, dialkylaminosulfonyl or sulfo; and $R^5$ is hydrogen, alkyl or amino.

8. A compound represented by the general formula (6) or a pharmaceutically acceptable salt or metal complex thereof:

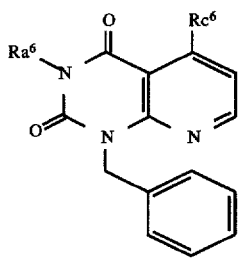

(6)

wherein $Ra^6$ is hydrogen or alkyl; and $Rc^6$ is amino, alkylamino or benzylamino.

9. A compound represented by the general formula (7) or a pharmaceutically acceptable salt or metal complex thereof:

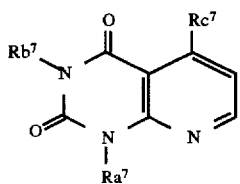

(7)

wherein $Ra^7$ and $Rb^7$ are the same or different and each of $Ra^7$ and $Rb^7$ is alkyl; and $Rc^7$ is acylamino, benzylamino or dialkylaminomethyleneamino.

10. A compound represented by the general formula (8) and a pharmaceutically acceptable salt thereof:

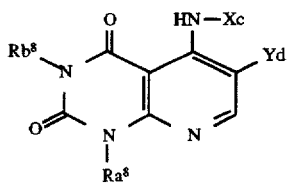

(8)

wherein $Ra^8$ and $Rb^8$ are the same or different and each of $Ra^8$ and $Rb^8$ is alkyl; Xc is hydrogen, alkyl or acyl; and Yd is alkyl, halogen, nitro, amino, hydroxyl, benzyloxy, carboxyl, alkoxycarbonyl, alkoxysulfonyl, aminosulfonyl, dialkylaminosulfonyl or sulfo.

11. A method of dilating the contracted bronchus and of remedying the laboring breath of bronchial asthma comprising administering to a patient having a contracted bronchus a pharmaceutically effective amount of at least one compound, salt, or metal complex of claim 6 which directly acts on the contracted tracheal smooth muscle to relax it and remedy the laboring breath of bronchial asthma.

12. A method as claimed in claim 1 wherein $R^1$ and $R^2$ may be the same or different and each of $R^1$ and $R^2$ is hydrogen or ethyl.

13. A method of dilating the contracted bronchus and of remedying the laboring breath of bronchial asthma comprising administering to a patient having a contracted bronchus a pharmaceutically effective amount of at least one compound, salt, or metal complex of claim 8 which directly acts on the contracted tracheal smooth muscle to relax it and remedy the laboring breath of bronchial asthma.

14. A method of dilating the contracted bronchus and of remedying the laboring breath of bronchial asthma comprising administering to a patient having a contracted bronchus a pharmaceutically effective amount of at least one compound, salt, or metal complex of claim 9 which directly acts on the contracted tracheal smooth muscle to relax it and remedy the laboring breath of bronchial asthma.

15. A method as claimed in claim 1 wherein $R^5$ is alkyl.

16. A method as claimed in claim 12 wherein $R^5$ is alkyl.

17. A method as claimed in claim 1 wherein one of $R^1$ and $R^2$ is hydrogen and the other is alkyl.

18. A method of dilating the contracted bronchus and of remedying the laboring breath of bronchial asthma comprising administering to a patient having a contracted bronchus a pharmaceutically effective amount of at least one compound, salt, or metal complex of claim 3 which directly acts on the contracted tracheal smooth muscle to relax it and remedy the laboring breath of bronchial asthma.

19. A method of dilating the contracted bronchus and of remedying the laboring breath of bronchial asthma comprising administering to a patient having a contracted bronchus a pharmaceutically effective amount of at least one compound, salt, or metal complex of claim 5 which directly acts on the contracted tracheal smooth muscle to relax it and remedy the laboring breath of bronchial asthma.

20. A method as claimed in claim 18 wherein $R^3$ is —NH—X.

* * * * *